(12) United States Patent
Vanpoucke et al.

(10) Patent No.: US 12,214,203 B2
(45) Date of Patent: Feb. 4, 2025

(54) DETECTION AND TREATMENT OF NEOTISSUE

(71) Applicant: Cochlear Limited, Macquarie University (AU)

(72) Inventors: Filiep Vanpoucke, Macquarie University (AU); Floris Heutink, Macquarie University (AU); Berit Verbist, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 259 days.

(21) Appl. No.: 17/636,665

(22) PCT Filed: Sep. 22, 2020

(86) PCT No.: PCT/IB2020/000768
§ 371 (c)(1),
(2) Date: Feb. 18, 2022

(87) PCT Pub. No.: WO2021/059016
PCT Pub. Date: Apr. 1, 2021

(65) Prior Publication Data
US 2022/0273951 A1    Sep. 1, 2022

Related U.S. Application Data

(60) Provisional application No. 62/904,069, filed on Sep. 23, 2019.

(51) Int. Cl.
*A61N 1/05* (2006.01)
*A61N 1/36* (2006.01)

(52) U.S. Cl.
CPC ....... *A61N 1/36139* (2013.01); *A61N 1/0541* (2013.01); *A61N 1/3614* (2017.08)

(58) Field of Classification Search
CPC .............. A61N 1/36139; A61N 1/0541; A61N 1/3614; A61N 1/37; A61N 1/3925;
(Continued)

(56) References Cited

U.S. PATENT DOCUMENTS 6,304,787 B1    10/2001  Kuzma et al.
7,860,573 B2    12/2010  van den Honert
(Continued)

FOREIGN PATENT DOCUMENTS

KR    10-1812492 B1    12/2017
WO    2019-136218 A1    7/2019

OTHER PUBLICATIONS

International Search Report and Written Opinion in counterpart International Application No. PCT/US2020/000768, mailed Jan. 29, 2021, 9 pages.
(Continued)

*Primary Examiner* — Carl H Layno
*Assistant Examiner* — Anh-Khoa N Dinh
(74) *Attorney, Agent, or Firm* — Edell, Shapiro & Finnan, LLC

(57) ABSTRACT

Disclosed examples include technology for the detection and treatment of neotissue formation proximate an implantable stimulator. Neotissue formation can include ossification, scar tissue, soft tissue fibrosis, and other tissue growth. The neotissue formation can be detected by analyzing (e.g., using a machine-learning framework) stimulation data relating to the implantable stimulator. Neotissue formation characteristics can be analyzed to determine appropriate treatment actions for ameliorating the effects of neotissue formation.

19 Claims, 6 Drawing Sheets

(58) Field of Classification Search
CPC ........ A61N 1/08; A61N 1/0464; A61N 1/375;
A61N 1/05; A61N 1/323; A61N 1/36038;
A61L 27/56; A61L 27/50; A61L 27/60;
A61L 2430/02; A61L 27/16; A61L 27/18;
A61L 27/38; A61L 27/3895; B33Y 30/00;
B33Y 50/00; B33Y 80/00; B33Y 70/00;
B33Y 10/00; B33Y 50/02; B33Y 70/10;
B29C 64/135; B29C 64/129; B29C
64/386; B29C 64/124; B29C 64/165;
B29C 64/393
See application file for complete search history.

(56) References Cited

U.S. PATENT DOCUMENTS

| | | | | |
|---|---|---|---|---|
| 2006/0247735 | A1* | 11/2006 | Honert | A61N 1/323 607/57 |
| 2006/0265025 | A1* | 11/2006 | Goetz | A61N 1/37 607/48 |
| 2010/0191089 | A1 | 7/2010 | Stebler et al. | |
| 2011/0257702 | A1 | 10/2011 | Kara et al. | |
| 2012/0300953 | A1* | 11/2012 | Mauch | H04R 25/554 381/60 |
| 2013/0331779 | A1* | 12/2013 | Dhanasingh | A61M 31/002 604/93.01 |
| 2016/0310738 | A1 | 10/2016 | Mauch et al. | |
| 2017/0165487 | A1 | 6/2017 | van den Honert | |
| 2018/0280687 | A1 | 10/2018 | Carter et al. | |
| 2019/0083544 | A1 | 3/2019 | Athanasiou et al. | |
| 2020/0238002 | A1 | 7/2020 | Heasmean et al. | |
| 2021/0093852 | A1 | 4/2021 | Heasmean et al. | |

OTHER PUBLICATIONS

Vanpoucke FJ, Zarowski AJ, Peeters SA, "Identification of the impedance model of an implanted cochlear prosthesis from intracochlear potential measurements", IEEE Transactions on Biomedical Engineering (vol. 51, Issue: 12, Dec. 2004).

Vanpoucke FJ, Boermans PP, Frijns JH, "Assessing the placement of a cochlear electrode array by multidimensional scaling", IEEE Transactions on Biomedical Engineering (vol. 59, Issue: 2, Feb. 2012).

Heutink F, Huinck W, Mens L, Vart P, Verbist B, Mylanus E, "The Influence of New Bone Formation After Cochlear Implant Surgery on Electrode Impedances, Intracochlear Voltage Distribution and Loss of Residual Hearing", OMAI, Oct. 2018, Tel Aviv.

Kamakura T, Nadol JB Jr., "Correlation between word recognition score and intracochlear new bone and fibrous tissue after cochlear implantation in the human", Hear Res. Sep. 2016; 339:132-41.

* cited by examiner

DETECTION AND TREATMENT OF NEOTISSUE

This application is being filed on Sep. 22, 2020, as a PCT International Patent application and claims priority to U.S. Provisional patent application Ser. No. 62/904,069, filed Sep. 23, 2019, the entire disclosure of which is incorporated by reference in its entirety.

BACKGROUND

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions and/or recipient monitoring for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical device.

SUMMARY

In an example, there is an apparatus comprising: a stimulator assembly having one or more electrodes; a biocompatible housing connected to the stimulator assembly; a stimulation source disposed in the biocompatible housing and configured to deliver electrical stimulation to target tissue of a recipient via the one or more electrodes; and one or more processors. The one or more processors are configured to: generate a current flow path using the one or more electrodes for stimulating tissue; measure one or more characteristics relating to the current flow path to generate stimulation data; determine neotissue formation characteristics relating to tissue growth proximate the one or more electrodes; determine a treatment modification instruction to modify stimulation parameters to account for the tissue growth; and apply the treatment modification instruction to modify ongoing stimulation provided by the apparatus.

In another example, there is a method comprising: determining a transimpedance matrix for a plurality of electrodes of an implanted stimulator; detecting neotissue formation characteristics proximate at least one of the plurality of electrodes based on the transimpedance matrix; performing a treatment action based on the neotissue formation characteristics.

In yet another example, there is a system comprising: one or more processors; a non-transitory computer-readable memory comprising instructions. The instructions, when executed by the one or more processors, cause the one or more processors to: determine neotissue formation characteristics relating to tissue growth proximate one or more electrodes of an implanted stimulator; determine a treatment modification instruction to modify stimulation parameters of the implanted stimulator to account for the tissue growth; and apply the treatment modification to the implanted stimulator to modify ongoing stimulation provided by the implanted stimulator.

BRIEF DESCRIPTION OF THE DRAWINGS

The same number represents the same element or same type of element in all drawings.

DETAILED DESCRIPTION

Figure 1:
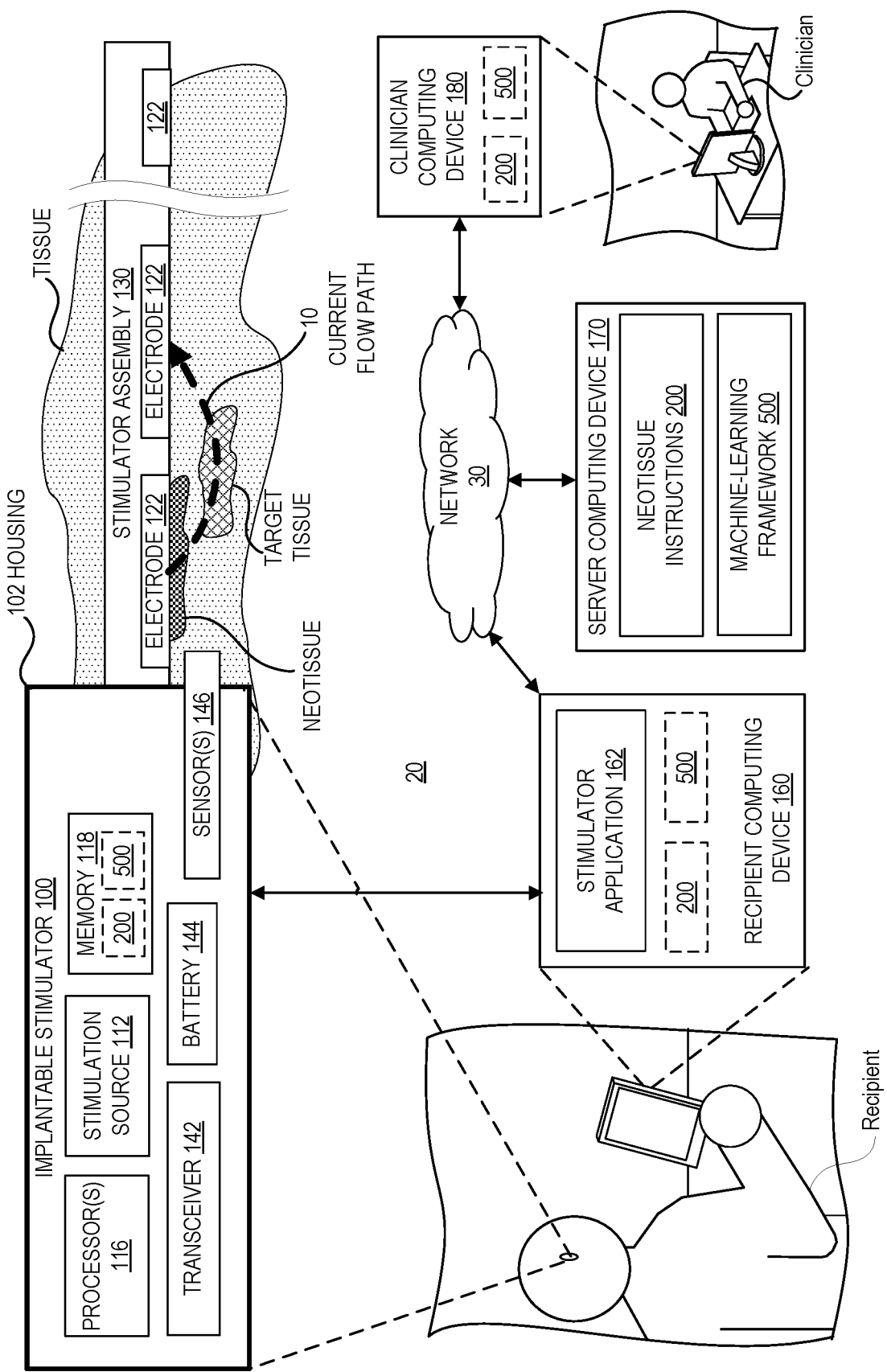
FIG. 1 is a functional diagram of a system having an implantable stimulator that can benefit from technology herein.

This application relates to the detection and treatment of neotissue formation proximate an implantable stimulator. The term "neotissue" can refer to ossification, scar tissue, soft tissue fibrosis, and other tissue growth proximate an implanted stimulator or a portion thereof formed after implantation of the stimulator. The neotissue can be formed via a natural or iatrogenic process. Iatrogenic neotissue formation proximate electrodes of an implantable stimulator can occur due to, for example, trauma during implantation of a stimulation assembly of the stimulator. Natural scar tissue can form as a reaction by the recipient's body to the presence of a foreign substance. For example, scar tissue can form to encapsulate the foreign substance. Within the context of cochlear implants, a common spot for neotissue formation is near the basal end of a stimulator assembly in close proximity to a cochleostomy site.

Sufficient formation of neotissue proximate an implanted stimulator (and particularly electrodes thereof) can affect the capability of the stimulator to provide effective therapeutic stimulation to the recipient. For example, stimulation current may have difficulty passing through the neotissue, which can create high contact impedance (e.g., resistive and capacitive) and monopolar tissue impedances. This change in the electrical properties of the stimulation path can result in higher power consumption by the implanted stimulator as well as out-of-compliance issues. The neotissue can negatively affect device fitting and can result in, for example, higher comfort level thresholds, longer pulse widths, and generally poorer access to the tissue that is the target of stimulation (particularly in case of ossification). For example, the neotissue can cause a therapeutic current flow path to form between the electrode and the neotissue instead of flowing toward target tissue, thereby changing the local longitudinal versus transversal current flow (e.g., creating a tendency to cause longitudinal flow). Further, neotissue can affect current spread in tissue. Where the implanted stimulator is a cochlear implant, such current spread can cause an unwanted increase in channel interaction. In view of the foregoing, detection, control, and reduction in the formation of neotissue proximate an implantable stimulator can provide benefits in the treatment provided by implanted stimulators. However, absent high-power imaging techniques, clinicians are currently blinded to the presence of neotissue proximate an implantable stimulator.

Examples disclosed herein include processes for the detection of neotissue formation using data measured by the implantable stimulator itself. Such processes can be used to infer the presence of neotissue formation without necessitating the use of medical imaging. In an implementation, impedance and transimpedance values are measured and analyzed to infer the presence of neotissue. Impedance and transimpedance values have multiple components (e.g., contact impedance and tissue impedance, among others). One or more of the components of the impedance values can facilitate discrimination between electrode contacts with or without formation of neotissue, particularly ossification. For example, a total impedance measurement can be processed to determine separation between groups of electrodes having neotissue formation and those lacking neotissue formation based on a density of new bone formation around the electrode contacts. An example network representing contribution of various components to the impedance model of a cochlear implant is described in Vanpoucke et al., "Identification of the Impedance Model of an Implanted Cochlear Prosthesis from Intracochlear Potential Measurements", IEEE Trans Biomed Eng. 2004 Dec; 51(12):2174-83, which is hereby incorporated by reference in its entirety herein for any and all purposes.

Neotissue can be detected on an electrode-by-electrode basis to allow for targeted amelioration of the effects of neotissue. Such a process can produce metrics regarding the state of the implantable stimulator and components thereof (e.g., electrodes). Such metrics can be useful in, for example, monitoring neotissue formation over time and measuring the effect of treatment actions used to control the neotissue formation. Further, data regarding neotissue formation can be used to select different electrode types or coatings, different surgical techniques, or other changes to future procedures on the recipient or other recipients to better address potential neotissue formation.

The detection of neotissue can be performed using data analysis techniques to estimate or infer neotissue formation based on stimulation data or other information. In an example, the process can predict the presence of neotissue by thresholding relevant impedance values. For instance, there can be a threshold value indicating whether neotissue is detectable. One or more impedance values of the stimulation data can be compared to the threshold value. The threshold being satisfied indicates the presence of neotissue. In a further configuration, the process can predict various degrees and types of neotissue formation (e.g., differentiating between ossification and scar tissue formation). The processes can use not only monopolar measurements but, in addition or instead, use a full transimpedance matrix (e.g., measured at one or multiple times) to detect the presence of neotissue, as well as data from other sources not limited only to electrical data. Such data can include, for example, medical imaging data (e.g., high-powered medical imaging data or even lower powered medical imaging data than would otherwise be necessary to identify neotissue), device settings (e.g., the user may change settings over time to attempt to compensate for neotissue formation that affects the stimulation provided), hearing tests, user responses, clinical observations, neural responses, other data, and combinations thereof. Further, data taken over time can be used to identify neotissue formation. The data collected can be compared to data collected for other recipients of auditory prostheses, including those with and without known neotissue formation. For instance, data from many users can be stored at a server and used as a basis against which additional data can be compared.

The results of neotissue detection can be used to perform treatment actions, such as controlling the application of therapy to prevent or reduce tissue formation. Further treatment actions can include modifying parameters that control the treatment provided by the implantable stimulator, such as a threshold level, a comfort level, pulse width selection, electrode selection, or multipolar configuration selection. Further still, the detected neotissue characteristics can serve as an objective measure input to a stimulation map tuning engine. In addition, the tissue characteristics can be used to set expectations in the treatment context or monitor the state of the implanted stimulator in the home environment (e.g., to monitor residual hearing where the implanted stimulator is a cochlear implant). Techniques disclosed herein can be used in conjunction with any of a variety of implantable stimulators, an example of which is shown and described in FIG. 1.

Neotissue Treatment and Detection System

FIG. 1 illustrates a system 20 configured for the detection and treatment of neotissue proximate an implantable stimulator 100. The system 20 can further include a recipient computing device 160, a server computing device 170, and a clinician computing device 180 connected over a network 30.

The network 30 is a computer network, such as the Internet, that facilitates the electronic communication of data among computing devices connected to the network 30.

The implantable stimulator 100 is a medical device implantable in a recipient and configured to provide therapeutic stimulation. The implantable stimulator 100 can take any of a variety of different forms, such as a cochlear implant, an electroacoustic hearing device, a sleep apnea stimulator, a neurostimulator, a vestibular stimulation device, a tinnitus treatment device, a cardiac stimulator, other implantable stimulators, or combinations thereof. The implantable stimulator 100 can have one or more components disposed within a housing 102, as well as one or more components extending from or disposed outside of the housing 102. The housing 102 can be configured to be implantable in a human or animal recipient by having biocompatible properties, such as by being constructed from a biocompatible material. In the illustrated example, the implantable stimulator 100 includes a stimulation source 112, one or more processors 116, memory 118, a stimulator assembly 130, a transceiver 142, a battery 144, and one or more sensors 146, among other components.

The implantable stimulator 100 can include one or more hardware circuits that provide stimulator functionality. In many examples, the implantable stimulator 100 includes one or more components for receiving a signal and generating and controlling delivery of a stimulation signal via one or more electrodes 122 of the stimulator assembly 130 based on the signal. The implantable stimulator can include components for generating or controlling the delivery of the stimulation signals to the stimulator assembly 130.

The stimulation source 112 is a component that is configured to deliver electrical stimulation to target tissue of a recipient via the one or more electrodes 122. For example, the stimulation source 112 can generate electrical stimulation signals for use in stimulating target tissue. The stimulation source 112 can use or generate stimulation control signals to generate electrical stimulation signals for delivery to target tissue via the one or more electrodes 122. The stimulation provided can be, for example, monopolar, bipolar, or multi-polar electrical stimulation. In many examples, the stimulation source 112 includes a current source/sink that produces current pulses based on input received from a decoder. The stimulation source 112 can further include a voltage source.

The one or more processors 116 are one or more electronic components that perform functions. As implemented in the implantable stimulator 100, the one or more processors 116 can be configured (e.g., via hardware, software, firmware, or combinations thereof) to perform a variety of functions relating to the providing of therapeutic stimulation. For example, the one or more processors 116 can be configured to perform stimulation-related functions to control one or more components of the implantable stimulator 100. For instance, the one or more processors 116 can open or close switches to control the flow of stimulation to the one or more electrodes 122. The one or more processors 116 can include one or more microprocessors configured to receive input and produce output based thereon (e.g., typically controlling one or more aspects or operations of the implantable stimulator 100). The one or more processors 116 can include one or more application-specific integrated circuits or field programmable gate arrays. The one or more processors 116 can be configured to perform operations relating to the detection or treatment of neotissue. In some examples, the one or more processors 116 can be configured by executing instructions (e.g., as stored in the memory 118) that cause the one or more processors 116 to perform one or more operations. The one or more processors can be one or more central processing units.

The memory 118 can be or include one or more software- or hardware-based processor-readable (e.g., computer-readable) storage media operable to store information (e.g., data or instructions) accessible by the one or more processors 116. The memory 118 can store, among other things, instructions executable by the one or more processors 116 to cause performance of operations described herein, as well as other information. The memory 118 can be volatile memory (e.g., RAM), non-volatile memory (e.g., ROM), or combinations thereof. The memory 118 can include transitory memory or non-transitory memory. The memory 118 can also include one or more removable or non-removable storage devices. In examples, the memory 118 can include RAM, ROM, EEPROM (Electronically-Erasable Programmable Read-Only Memory), flash memory, optical disc storage, magnetic storage, solid state storage, or any other memory media usable to store information for later access. In examples, the memory 118 encompasses a modulated data signal (e.g., a signal that has one or more of its characteristics set or changed in such a manner as to encode information in the signal), such as a carrier wave or other transport mechanism and includes any information delivery media.

The stimulator assembly 130 includes the one or more components of the implantable stimulator 100 for delivering stimulation signals to target tissue. In many examples, the stimulator assembly 130 includes an elongate lead on or in which the one or more electrodes 122 are disposed. The lead can be configured to place and hold the electrodes 122 into contact with a desired location proximate target tissue for providing stimulation. In some examples, the electrodes 122 can be used to not only provide stimulation, but also act as sensors that can sense data. In other examples, the implantable stimulator 100 includes separate stimulation and sensing electrodes 122. Where the implantable stimulator 100 is a cochlear implant, the stimulator assembly 130 can take the form of (or have one or more characteristics or components of) the carrier members described in U.S. Pat. No. 8,249,724, which is titled "Elongate implantable carrier member having an embedded stiffener" and which is hereby incorporated by reference herein in its entirety for any and all purposes.

The transceiver 142 is a component configured to transmit and/or receive signals to/from another component through a wired or wireless communication. For example, the transceiver 142 can be configured to transcutaneously receive a power signal and/or a data signal from an external processor or charger device (not shown). The transceiver 142 can be a collection of one or more implanted components that form part of a transcutaneous energy or data transfer system. Further, transceiver 142 can include any number of components that receive or transmit a power signal or data signal, such as a coil for a magnetic inductive arrangement, an antenna for an alternative RF system, capacitive plates, or any other suitable arrangement. Various types of energy transfer, such as electromagnetic, capacitive, and inductive transfer, can be used to usably receive the power signal and/or the data signal from the external processor device at the implantable stimulator 100.

The battery 144 is a component configured to store power and provide power to the other components of the stimulator device 501 as needed for operation. The battery 144 can include, for example, one or more rechargeable batteries. Power can be received from an external device, such as an external processor device or external charger device, and stored in the battery 144. In other examples, the implantable stimulator 100 can include an energy scavenging component to charge the battery 144.

The one or more sensors 146 are components configured to produce data based on measurements. Any of a variety of sensors 146 can be used. The sensors 146 can include not only sensors placed proximate the target tissue, but also sensors 146 located elsewhere. For instance, where the implantable stimulator 100 is a cochlear implant, there can be sensors located within the cochlea (e.g., intracochlear sensors, such as electrodes configured to sense data), as well as outside of the cochlea (e.g., extracochlear sensors, such as extracochlear electrodes). In some examples, the sensors 146 can include brain scalp leads. The sensors 146 can also include one or more accelerometers, gyroscopic sensors, location sensors, telecoils, biosensors (e.g., heart rate or blood pressure sensors), and light sensors, among others. The sensors 146 can include components disposed within a housing of the implantable stimulator 100 as well as devices electrically coupled to implantable stimulator 100 (e.g., via wired or wireless connections). The sensors 146 can further include sensors that obtain data regarding usage of the implantable stimulator 100, such as software sensors operating on the implantable stimulator 100 that tracks: when the implantable stimulator 100 is used, when one or more of the implantable stimulator settings are modified, and for how long the implantable stimulator is operated using particular settings, among other data. In some examples, one or more of the sensors 146 can be configured to measure large technical potentials (e.g., having an order of magnitude in volts), and/or one or more of the sensors 146 can be configured to measure small biological potentials (e.g., having an order of magnitude in the micro- to millivolt range).

In examples, the implantable stimulator 100 (e.g., the one or more processors 116 thereof) periodically obtains readings from the sensors 146. In other examples, the implantable stimulator 100 (e.g., the one or more processors 116 thereof) obtains the readings responsive to an external request (e.g., a request received from the recipient computing device 160, such as from the stimulator application 162 thereof) or an internal request (e.g., a request generated from a program running on the one or more processors 116). In examples, the data not only includes the data itself, but also metadata, such as time period data regarding when (e.g., time of day) the data was obtained. Such data can facilitate the tracking of changes in data over time that can be useful in identifying neotissue formation.

As illustrated, the implantable stimulator 100 generated a current flow path 10 from one electrode 122 to another electrode 122. Although the illustration is of a bipolar current flow path 10 between implanted electrodes 122, the current flow path 10 can take other forms. For example, the current flow path 10 can be monopolar or multi-polar, among other forms. The current flow path 10 can be generated to provide stimulation to target tissue of a recipient. Further, the current flow path 10 can pass through neotissue.

In some examples, one or more components of the implantable stimulator 100 can be housed in an external device wearable by the recipient. The external device can be configured to be in communication with the implantable stimulator 100 to, for example, transmit power or data to the implantable stimulator 100. Where the implantable stimulator is a cochlear implant, the external device can take the form of a button sound processor worn on the recipient's head. Further, the implantable stimulator 100 can be associated with one or more auxiliary devices. An example implementation of an implantable stimulator having one or more external devices and one or more auxiliary devices is described in U.S. Provisional Patent Application No. 62/824,433, which is titled "Auxiliary Device Connection" and which is hereby incorporated by reference in its entirety herein for any and all purposes.

The recipient computing device 160 is a computing device associated with the recipient of the implantable stimulator 100. In many examples, the recipient computing device 160 is a phone, watch, tablet computer, desktop computer or another consumer device, but the recipient computing device 160 can take other forms. For example, the recipient computing device 160 can include a device for use by the recipient in operating the implantable stimulator 100. As illustrated, the recipient computing device 160 can include a stimulator application 162.

The stimulator application 162 is a software application that operates on the recipient computing device 160 and cooperates with the implantable stimulator 100 (in some examples, via an external device, such as a wearable sound processor where the implantable stimulator 100 is a cochlear implant). For instance, the stimulator application 162 can control the implantable stimulator 100 (e.g., based on input received from the recipient), monitor usage of the implantable stimulator 100, and obtain data from the implantable stimulator 100. The recipient computing device 160 can connect to the implantable stimulator 100 using, for example, a wireless radiofrequency communication protocol (e.g., BLUETOOTH). The stimulator application 162 can transmit or receive data from the implantable stimulator 100 over such a connection. The stimulator application 162 can provide visual or audio alerts to the recipient on conditions of the implantable stimulator 100 (e.g., alerts relating to the formation of neotissue). The stimulator application 162 can facilitate the communication of data from the implantable stimulator 100 to another device, such as the server computing device 170 or the clinician computing device 180.

The server computing device 170 is a server remote from the implantable stimulator 100, recipient computing device 160, and the clinician computing device 180. The server computing device 170 can be communicatively coupled to the recipient computing device 160 and the clinician computing device 180 over the network 30. In many examples, the server computing device 170 is indirectly communicatively coupled to the implantable stimulator 100 through the recipient computing device 160 (e.g., via the stimulator application 162). In some examples, the server computing device 170 is directly communicatively coupled to the implantable stimulator 100. The server computing device 170 can include neotissue instructions 200 and a machine-learning framework 300, which are described in more detail in FIG. 2 and FIG. 3, respectively. In addition to or instead of the server computing device 170 including the neotissue instructions 200 and the machine-learning framework 300, the implantable stimulator 100, recipient computing device 160, and clinician computing device 180 can include the neotissue instructions 200 and the machine-learning framework 300.

The clinician computing device 180 is a computing device used by a clinician. A clinician is a medical professional, such as a medical professional that provides, maintains, or supports the implantable stimulator 100. In an example, the clinician is a medical professional that provides care or supervision for the recipient. The clinician computing device 180 can include one or more software programs usable to monitor, program, or support the implantable stimulator. In examples, the clinician computing device 180 can provide visual or audio alerts to the clinician based on conditions of the implantable stimulator 100 (e.g., alerts relating to the formation of neotissue).

One or more components of the system 20 can individually or collectively perform processes relating to the detection and treatment of neotissue affecting the implantable stimulator 100. An example of such a method is described in relation to FIG. 2.

Example Method

Figure 2:
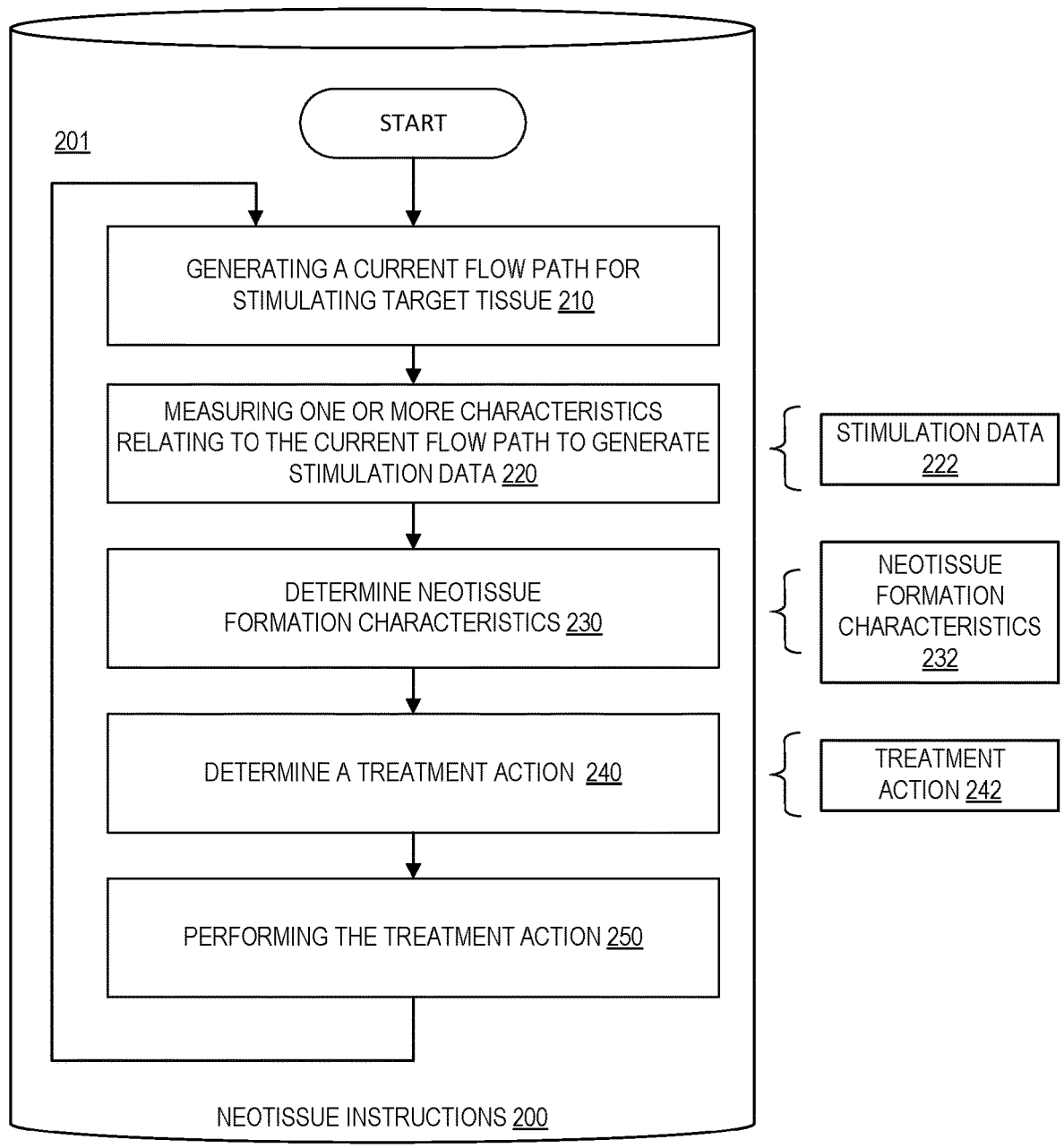
FIG. 2 illustrates neotissue instructions implementing an example process relating to the detection and treatment of neotissue affecting an implantable stimulator.

FIG. 2 illustrates neotissue instructions 200 implementing an example method 201 relating to the detection and treatment of neotissue affecting an implantable stimulator 100. In some examples, one or more operations of the method 201 can be performed via the execution of the computer-executable instructions 200 by one or more processors. The method 201 can begin with operation 210.

Operation 210 includes generating or causing to be generated a current flow path 10 using one or more of the electrodes 122 of the implantable stimulator 100. The current flow path 10 is the path that current takes during stimulation, such as from an active electrode to a return electrode. In many examples, the implantable stimulator 100 is configured to produce a current flow path 10 to stimulate particular target tissue. The current flow path 10 can pass through not only the target tissue but also tissue proximate the target tissue and the implantable stimulator 100. Formation of neotissue proximate the electrodes 122 of the implantable stimulator 100 can affect the current flow path 10 and the provided stimulation.

The generating of the current flow path 10 can include generating a therapeutic stimulation current flow path or generating a diagnostic stimulation current flow path. For example, where the method 201 is at least partially being performed during therapeutic use of the implantable stimulator, operation 210 can include generating a therapeutic stimulation current flow path 10. The therapeutic stimulation current flow path 10 is a current flow path 10 having a primary purpose of providing therapeutic stimulation to a recipient of the implantable stimulator 100. For example, where the implantable stimulator 100 is a cochlear implant, the therapeutic stimulation current flow path can be a current flow path 10 configured to cause a hearing percept in the recipient (typically based on sound input). As another example, where the implantable stimulator 100 is a vestibular stimulation system, the current flow path can be a current flow path configured to cause a vestibular percept in the recipient. As an alternative to the therapeutic stimulation current flow path 10, the current flow path 10 can be a diagnostic stimulation current flow path 10. The diagnostic stimulation current flow path 10 can be a current flow path 10 generating primarily for diagnostic purposes (e.g., to determine an extent or effect of neotissue formation) rather than therapeutic stimulation purposes.

Whether the current flow path 10 is a therapeutic or diagnostic stimulation current flow path 10, the current flow path 10 can be generated by the stimulation source 112. The current flow path can be generated in any of a variety of ways depending on the configuration of the implantable stimulator. In examples, the current flow path 10 monopolar, bi-polar, or multipolar stimulation. Example implantable stimulators and techniques and electronics for generating the current flow path 10 can be the same as or incorporate aspects of those techniques described in U.S. Pat. No. 4,408,608, entitled "Implantable Tissue Stimulating Prosthesis" and U.S. Pat. No. 8,583,246, entitled "Cochlear Implant with Deactivation System", which are both incorporated by reference in their entirety herein for any and all purposes. During or following operation 210, the flow of the method 201 can move to operation 220.

Operation 220 includes measuring one or more characteristics relating to the current flow path 10 to generate stimulation data 222. As described in more detail below, measuring the characteristics can include generating various kinds of stimulation data 222, such as voltage profile data, transimpedance matrix data, non-biological measurements (e.g., intracochlear voltages induced by the current flow where the implantable stimulator 100 is a cochlear implant), biological potential data, electrical field imaging data, electrical sounding data, other data, or combinations thereof. While some of the stimulation data 222 relates directly to characteristics of the current flow path 10 itself, other data can be obtained that, while not necessarily obtained during or as a result of stimulation, can nonetheless relate to the capability of the implantable stimulator 100 to provide stimulation. Further, the stimulation data 222 need not include only data obtained during stimulation, but can also include data relating to already-provided stimulation. The stimulation data 222 can be obtained using any of a variety of sensors or data sources of the implantable stimulator 100. In many examples, the electrodes 122 of the implantable stimulator can act as not only sources of stimulation but also sources of data.

In an example, the stimulation data 222 includes a voltage profile and the operation 220 includes obtaining a voltage profile. A voltage profile is a measurement of voltage at one or more electrodes of the implantable stimulator 100 in response to the application of current at one or more electrodes 122, such as a result of generating the current flow path 10. For example, the voltage profile can reflect the voltage created at different nerve regions of the tissue (e.g., "tissue voltage") at a plurality of locations proximate electrodes 122 of the stimulator assembly 130 in response to current delivered to a particular electrode 122. In an example implementation, the implantable stimulator 100 has twenty-two electrodes, and current delivered by electrode eleven can spread over a potentially wide spatial extent of neighboring tissue regions. This current spread may extend, for example, to nerve regions proximate distant electrodes 122 one and twenty-two of the twenty-two electrodes 122 of the example stimulator assembly 130. As a result, the voltage profile can indicate voltage not only proximate the eleventh electrode 122, but also proximate other electrodes 122. In the example, the stimulating voltage would likely be strongest proximate the eleventh electrode 122 and gradually decline proximate other electrodes 122. The voltage profiles for an implantable stimulator 100 can vary over time and neotissue can affect the voltage profiles. For example, relative differences in voltage measurement from one electrode to another or differences in one electrode over time can indicate the formation of neotissue proximate an electrode 122 producing an outlier value. Example voltage profiles are shown and described in relation to FIGS. 1 and 2 of U.S. Pat. No. 7,860,573, which is titled "Focused Stimulation in a Medical Stimulation Device" and which is hereby incorporated by references in its entirety for any and all purposes.

In an example, the stimulation data 222 includes a transimpedance matrix and the operation 220 includes determining a transimpedance matrix for the plurality of electrodes 122 of the implantable stimulator 100. An example transimpedance matrix, $Z_m$, is shown below:

$$Z_m = \begin{bmatrix} Z_{1,1} & \cdots & Z_{1,n} \\ \vdots & \ddots & \vdots \\ Z_{n,1} & \cdots & Z_{n,n} \end{bmatrix}$$

The transimpedance matrix $Z_m$ has n columns and n rows, where n is the number of electrodes 122 of the implantable stimulator 100. Each column and row corresponds to a particular electrode of a stimulator assembly 130 array comprising n electrodes 122, where a row corresponds to the electrode 122 on which stimulation is applied in measuring the transimpedance matrix. The value of n can vary depending on the configuration of the implantable stimulator 100. In an example, n can be twenty-two. Columns in the transimpedance matrix correspond to the electrode 122 on which the applied stimulation is measured in obtaining the transimpedance matrix. All values, except the diagonal, of the transimpedance matrix can be empirically measured by stimulating each electrode with a known current, one at a time. Then, the resulting voltage at each non-stimulated electrode is measured. Because voltage observed on the stimulating electrode includes parts from the bulk resistance and tissue impedance, the diagonal of the transimpedance matrix is not determined in this manner. Rather, the values along the diagonal ($Z_{1,1}$ to $Z_{n,n}$) of transimpedance matrix can be estimated by linear extrapolation or interpolation of the values surrounding the diagonal values.

A transimpedance matrix can be measured in any of a variety of ways. In an example, polarity of current flow is used. In an example, monopolar stimulation is used, and in other examples a four-point impedance or alternative bipolar measurements can be used. Various routings of the current flow can be used. In another example, phase width timing can be used. Transimpedance measurements can be taken at several points in time, ranging from the start of the first phase of a stimulation pulse to the end of the second phase of the stimulation pulse. In an example, multiple transimpedance matrices can be measured, with a transimpedance matrix being measured at multiple times during a stimulation pulse (e.g., early in the pulse and late in the pulse). Such measurement can be useful in separating capacitive and resistive components, and therefore separate contact impedance contributions from tissue impedance contributions, which can contribute to more accurate neotissue formation determinations. In addition or instead, measuring the one or more transimpedance matrices can include measuring transimpedance matrices longitudinally (e.g., over a time period longer than a single stimulation pulse, such as daily, weekly, or monthly). Such longitudinal measurements can be used to track the evolution of data over time to facilitate monitoring for changes caused by neotissue formation.

When measuring on the stimulation contact, this configuration allows voltage buildup over the stimulating contact (contact impedance) to be characterized and separate the impedance component, due to the contact, from the impedance components relating to the flow of the current through the cochlear tissues and back to the reference electrode. In yet another example, stimulus intensity can be used. The contact impedance can be non-linear with current intensity, and the tissue resistivity can be linear. The use of stimulus intensity can facilitate separating a linear tissue component and a non-linear contact impedance component. The values of the measured transimpedance matrix can be affected by the presence or absence of neotissue. Additional details and example implementations of obtaining a transimpedance matrix are described in U.S. Pat. No. 7,860,573, which was previously incorporated herein by reference for any and all purposes.

In examples, the stimulation data 222 includes non-biological measurements (e.g., the intracochlear voltages induced by the current flow) and biological potentials, such as the action potentials generated by a stimulated nerve. Evoked compound action potentials are neural responses to the stimulation. The nerve cells that are activated by electrical stimulation emit an action potential a little later in response to the stimulus. This biological response is recordable by the implant. Where the implantable stimulator is a cochlear implant, neural response telemetry can be used to obtain data regarding electrical field that reaches the auditory nerve. In an example, the neural response data can be obtained using a measurement of evoked neural response technique described in U.S. Pat. No. 8,454,529, which is titled "Minimization of Electrical Stimulus Artifact during Measurement of Evoked Neural Response" and which is hereby incorporated by reference in its entirety for any and all purposes. The presence of neotissue can affect the ability of an electrical field to reach a nerve, so non-biological measurements and biological potentials can be affected by the presence of neotissue.

In an example, the stimulation data 222 includes electrical field imaging data, and the operation 220 can include obtaining electrical field imaging data. To obtain electrical field imaging data, the implantable stimulator can stimulate an electrode 122 and record the decay of the electrical potential along the tissue on additional electrodes 122. Then, the set of electrical spread curves that results can be analyzed to infer electrode trajectory. The presence of neotissue can affect electrode trajectory, thus the electrical field imaging data can be used to infer the presence of neotissue. Additional details regarding the obtaining of electrical field imaging data is described in Vanpoucke et al, "Assessing the Placement of a Cochlear Electrode Array by Multidimensional Scaling", 59 IEEE transactions on Biomedical Engineering 2 (February 2012) and Vanpoucke et al, "Identification of the Impedance Model of an Implanted Cochlear Prosthesis From Intracochlear Potential Measurements", 51 IEEE transactions on Biomedical Engineering 12 (December 2004), which are both hereby incorporated by reference in their entirety for any and all purposes.

In an example, the stimulation data 222 includes electrical sounding data and the operation 220 can include obtaining electrical sounding data. An example of electrical sounding techniques are described in U.S. 2018/0280687, which is titled "Advanced Electrode Array Insertion and Position Management", and which is hereby incorporated by reference in its entirety for any and all purposes. While that publication describes the use of electrical sounding in determining positioning of an electrode array of a cochlear implant, the same or similar techniques can be used to generate electrical sounding data useful in determining the presence of neotissue proximate implantable stimulators 100.

In examples, the stimulation data 222 can include data taken over time and the operation 220 can include obtaining data over time. For example, multiple transimpedance matrices can be obtained, such as an intra-operative transimpedance matrix and subsequent transimpedance matrices taken over time (e.g., weekly, monthly, yearly, or at other times). The inflammation process that can lead to electrode 122 encapsulation by neotissue can take at least four weeks to stabilize, but can take less or more time in some circumstance (e.g., due to secondary trauma caused by activation of electrical stimulation, encapsulation can stabilize later than four weeks). Thus, while initial stimulation data 222 might not indicate the presence of neotissue, subsequently obtained stimulation data 222 or changes over time in the stimulation data 222 might indicate neotissue formation.

Following operation 220, the flow of the method 201 can move to operation 230.

Operation 230 includes determining neotissue formation characteristics 232. The determining can be based on the stimulation data 222. The neotissue formation characteristics 232 can include data regarding the formation of neotissue proximate the implantable stimulator 100. The neotissue formation characteristics 232 can include data regarding the neotissue itself in addition to or instead of data regarding how the implantable stimulator 100 is affected by the neotissue. The neotissue formation characteristics 232 can include data regarding a location of the neotissue or the one or more electrodes 122 affected by the neotissue. The neotissue formation characteristics 232 can include data including the current flow paths 10 affected by the neotissue, target tissue affected by the neotissue, the amount of neotissue, the extent to which neotissue affects stimulation, other data, or combinations thereof.

In an example, the determining or detecting of the neotissue formation characteristics 232 can include determining a metric estimating an extent of tissue growth proximate one or more electrodes of the implanted medical stimulator. For example, the metric can be a score describing an extent to which one or more electrodes 122 are affected by neotissue formation. In addition or instead, the metric can be used to determine whether or how well one or more treatment actions have affected the neotissue. A scoring algorithm can obtain the stimulation data 222 as input and provide, as output, a metric for each of the electrodes describing an extent to which the electrode is predicted to be affected by neotissue formation. In an example, the output is calculated as being proportional to the extent to which the stimulation characteristics of the current flow paths 10 originating from or terminating at the electrode 122 have changed over time (e.g., negatively affected over time). In an example, the output is calculated by applying a statistical analysis to the input data.

Any of a variety of techniques can be used to determine the neotissue formation characteristics 232. In an example, relevant parameters can be extracted from the stimulation data 222 that are indicative of the local voltage field proximate one or more of the electrodes 122 (e.g., contact impedances and near-field tissue impedances). The indications of the local voltage field can be processed to generate neotissue formation characteristics 232. The indications and other relevant parameters can be analyzed by, for example, a classification algorithm that has been tuned or trained based on training sets of cases where neotissue formation occurred versus standard cases with minimal or no neotissue formation. In some examples, the classification algorithm is a thresholding algorithm that determines whether one or more values of the transimpedance matrix satisfy a threshold (e.g., by comparing the one or more values to one or more thresholds). If so, neotissue formation is detected. In other examples, the classification algorithm can take the form of a decision tree or neural network that receives a plurality of transimpedance matrix parameters and one or more additional parameters. Such an algorithm can implement a non-linear classification in a highly dimensional-space. Further still, statistical analyses of one or more aspects of the stimulation data 222 can be performed to determine the neotissue formation characteristics.

Other data can be used in addition to or instead of the stimulation data 222 to determine the neotissue formation characteristics 232. For example, anatomical data describing one or more characteristics of the recipient's anatomy can be obtained and used. Such data can include the size, shape, and orientation of the tissue proximate the target tissue. For instance, where the implantable stimulator 100 is a cochlear implant, such data can include characteristics of the cochlea. The anatomical data can further include actual or predicted electrical characteristics of the tissue proximate the electrodes 122.

Further, position data can be obtained and used. For example, the method 201 can further include determining a position of at least one electrode 122 of the implantable stimulator 100 using medical imaging data, and the operation 230 can further be based on the determined position. For instance, where the implantable stimulator is a cochlear implant, the position data can include data regarding the placement of the electrode, such as measurements regarding modiolar proximity or insertion length. The position data can be obtained from an imaging source, such as an x-ray image or an MRI image.

Further still, the implantable stimulator 100 can include one or more sensors, the output of which can analyzed as part of operation 230 to determine neotissue formation characteristics 232. For example, the one or more sensors can include an optical biosensor, an electrochemical biosensor, or a mass biosensor, among others. Such sensors can provide an electrical output representing a biological state proximate the implantable stimulator 100. For example, the optical biosensor can use light to extract data from physical properties of a target object, such as changes to the reflective index of a metal. The electrochemical biosensor is a device that employs one or more of potentiometry, amperometry, and conductometry to analyze the content of a biological sample. An optical biosensor or an electrochemical biosensor may be used to detect the presence or concentration of target molecules based on their spectral fingerprint. Such information can be used to assess the biological environment, presence of target molecules or conditions that may indicate the presence or absence of neotissue. The mass biosensor can use surface acoustic waves and piezoelectric effects for biosensing various parameters (e.g., metabolites, proteins, antigens, and microorganisms) that may indicate the presence or absence of neotissue. In accordance with embodiments presented herein, a mass biosensor may be used to quantify and detect changes to a biological environment proximate the implantable stimulator that can indicate the presence or absence of neotissue.

The determining of the neotissue formation characteristics can use the "raw" measured stimulation data 222 (e.g., transimpedance matrix data thereof). In addition or instead, the determining can be based on derived features from the stimulation data 222 (e.g., using electrical conduction model parameters determined based on the stimulation data 222). In a first approach, statistics (e.g., statistics relating to electrode 122 impedance parameters for normal electrodes 122 and electrodes 122 affected by neotissue) can be used to implement thresholds for separating normally-functioning electrodes from those affected by neotissue formation. In an example, a threshold of one or more values of the stimulation data 222 can be used to determine the presence or absence of neotissue formation. For instance, responsive to one or more values of the stimulation data 222 satisfying a threshold, the presence of neotissue can be inferred. In an example, a conduction model estimation can be used to extract useful features from the stimulation data 222 (e.g., the transimpedance matrix thereof) and the resulting network parameters can be used as input to a classifier (e.g., the machine learning framework 300). In another example, a longitudinal electrical field imaging measure can be analyzed (e.g., thresholded) to determine neotissue formation characteristics 232. In an example, the determining can include, a plurality of parameters extracted from a transimpedance matrix. The parameters can be combined non-linearly. For instance, a decision tree can be used. In another example, a probabilistic graphical model is used. In some examples, a neural network can be used.

Figure 3:
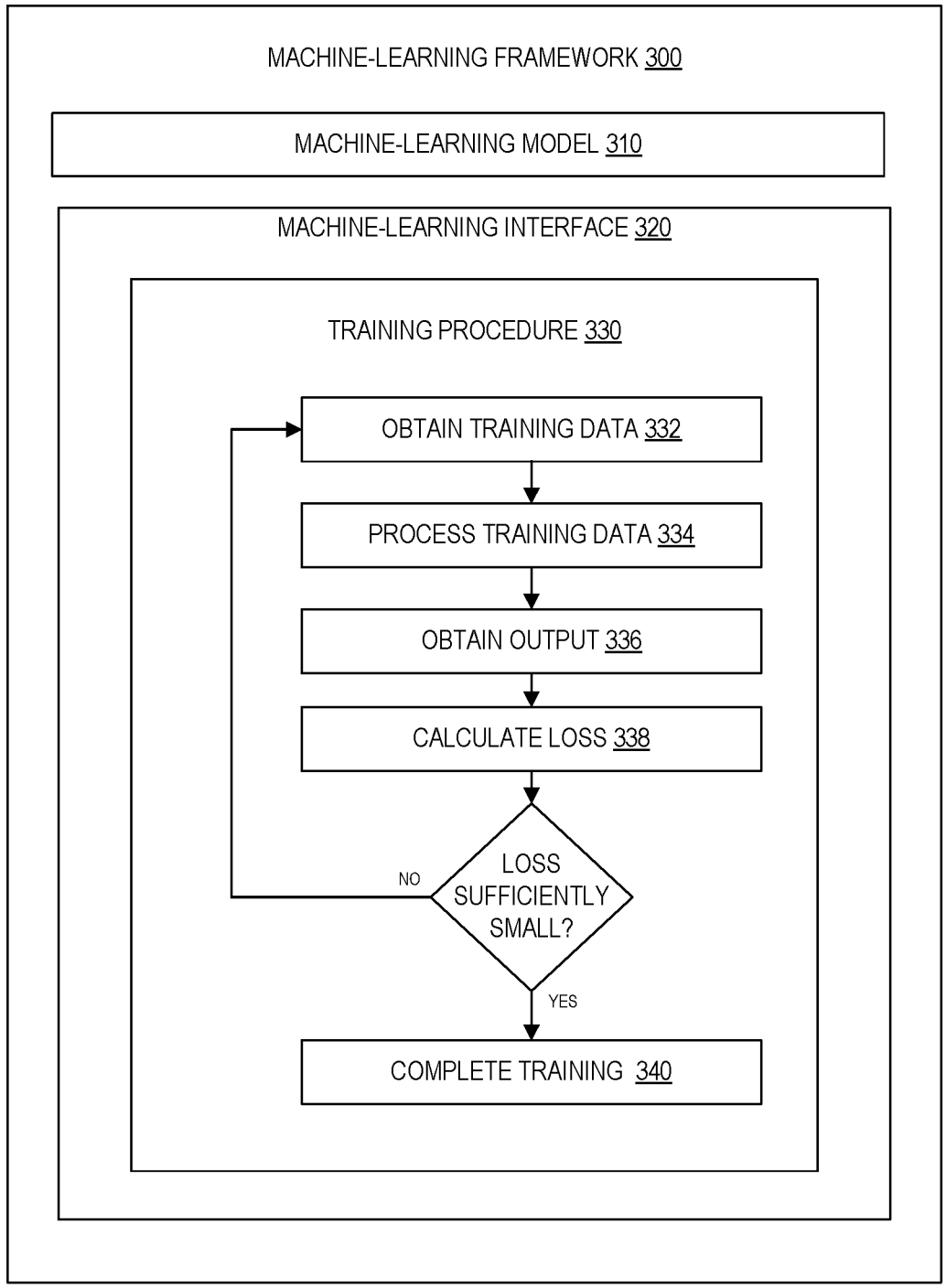
FIG. 3 illustrates an example machine-learning framework that may be used with examples herein.

In examples, the determining of the neotissue formation characteristics 232 can be performed using a machine-learning framework, such as the one described in relation to FIG. 3 herein. For example, some or all of the stimulation data 222 and other data can be provided as input into the machine-learning framework, the machine-learning framework can process the input, and provide an output that is or can be used as part of the neotissue formation characteristics 232. For example, a transimpedance matrix can be provided as input into the machine-learning framework, the machine-learning framework can process the transimpedance matrix, and the machine-learning framework can provide data as output that indicates a metric of neotissue formation proximate one or more of the electrodes 122. In an example, the resulting output can be a value expressing a confidence that one or more electrodes have neotissue formation (e.g., the confidence can be expressed as a value between 0 and 1).

Operation 240 includes determining a treatment action 242 (if any) to perform based on the neotissue formation characteristics 232. In some examples, if the neotissue formation characteristics 232 indicate that no neotissue has been formed or that no neotissue substantially affecting operation of the implantable stimulator 100 has been formed, then it may be determined that no treatment action 242 is necessary to perform. But if the neotissue formation characteristics 232 indicates that neotissue has been formed or that neotissue substantially affects operation of the implantable stimulator 100, then one or more treatment actions 242 can be selected and performed. Determining whether to perform a treatment action 242 and what treatment action 242 to perform (if any) can be accomplished in any of a variety of ways.

In examples, the determining can be performed using a decision tree, one or more thresholds, a heuristic technique, other techniques, or combinations thereof. For example, the determining can include determining an extent to which neotissue formation affects therapeutic stimulation provided by the implantable stimulator 100. Then, based on the extent, any of a variety of treatment actions 242 can be performed.

In an example, the treatment action 242 includes the application of a therapy to the recipient to affect neotissue formation. For example, the therapy can be selected to reduce or prevent future neotissue formation or reduce current neotissue. Such a therapy can include, pharmacological intervention, such as providing a therapeutically-effective amount of an anti-inflammatory drug to the recipient. The providing of the drug can reduce tissue growth or help resist the formation of unwanted tissue growth proximate the one or more electrodes 122. In some examples, the implantable stimulator 100 itself can be configured to provide a drug, such as by having a drug eluding material. In additional examples, the implantable stimulator 100 can include a drug-delivery pump or other mechanism that can be selectively activated to deliver anti-neotissue drugs in response to detecting the formation of neotissue. An example of such a delivery system is described in WO 2019/073348, which is entitled "Clinical-based Automated Delivery of Treatment Substances to the Inner Ear", and which is hereby incorporated by reference herein in its entirety for any and all purposes. In some examples, the therapy includes providing electrical stimulation using the implantable stimulator 100 in a manner configured to affect the neotissue formation, such as by damaging the neotissue. During or after the providing of the treatment action 242, neotissue formation characteristics 232 can continue to be monitored. For example, the neotissue formation characteristics 232 can be monitored to determine whether and to what extent the treatment action 242 is affecting neotissue formation.

In some examples, determining the treatment action 242 can include determining a modification instruction to modify provided stimulation parameters to account for tissue growth proximate the one or more electrodes. For example, it can be determined that the neotissue affects the performance of the implantable stimulator 100 and the treatment action 242 can include modifying the performance of the implantable stimulator 100 to ameliorate the effects of the neotissue. For example, modifying the performance of the implantable stimulator 100 can include modifying parameters of the stimulator device to affect ongoing operation of the implantable stimulator 100. In an example where the implantable stimulator 100 is a cochlear implant, the parameters to be modified can include a threshold level parameter or a comfort level parameter. The threshold level relates to a level of stimulation that needs to be provided to reach the recipient's threshold of hearing. The comfort level relates to a highest level of stimulation to be provided that is within a threshold of comfort for the recipient. Additional parameters include, auto pulse width selection parameters, electrode selection parameters, or multipolar configuration selection parameters. For example, where the neotissue reduces the amount of stimulation provided target tissue, the parameters of the implantable stimulator 100 can be modified (e.g., increased or decreased) to the point where the amount of stimulation provided to the target tissue is at a desired level. In another example, where the neotissue affects the current flow path 10, the different electrodes 122 by which particular treatments are provided can be changed to better shape the current flow path 10 to reach the target tissue. The treatment action 242 can include rerouting current flow for better neural access, such as by changing an amount of electrodes used in stimulation (e.g., changing among monopolar, bipolar, and multi-polar stimulation).

In an example, the treatment action 242 includes reporting a performance quality of the implantable stimulator 100 with respect to neotissue formation. For example, the device performing the operation 240 (e.g., the implantable stimulator 100, the recipient computing device 160, the server computing device 170, or the clinician computing device 180) can transmit or otherwise provide an alert to the clinician, the recipient, or another person indicating that the implantable stimulator may not be functioning as intended. For instance, the alert can be an art to the recipient (e.g., of the implantable stimulator 100, which can be an electroacoustic device) indicating a potential loss of residual hearing.

Following operation 240, the flow of the method 201 can move to operation 250.

Operation 250 includes performing the treatment action 242. In an example, this operation 250 includes applying the treatment modification instruction to modify ongoing stimulation. For example, where the treatment action 242 includes modifying threshold stimulation level parameters and maximum stimulation level parameters, operation 250 can include modifying a threshold stimulation level provided by the stimulation source 112 and modifying a maximum stimulation level provided by the stimulation source 112. The operation 250 can include providing a drug treatment, such as by activating a drug treatment feature of the implantable stimulator 100 (e.g., by activating a drug pump, exposing a drug eluding material to tissue, or via another technique). As another example, where the treatment action 242 is to disable one or more of the electrodes, performing the treatment action 242 can include disabling at least one of the one or more electrodes 122 (e.g., the at least one electrode is removed from use as part of normal stimulation) and the stimulation can be remapped to limit the effect of the disabled at least one electrode 122 on the ability of the implantable stimulator 100 to properly provide stimulation. In some examples, performing a treatment action 242 can include transmitting an instruction to the implantable stimulator 100 to modify ongoing operation of the implantable stimulator. In some examples, transmitting the instruction can include sending a command that, when performed by the implantable stimulator 100, modifies the operation of the implantable stimulator 100. In addition or instead, firmware of the implantable stimulator can be patched, flashed, or otherwise modified to affect ongoing operation of the implantable stimulator. The treatment action 242 can include reprogramming some or all of the implantable stimulator 100.

Example Machine-Learning Framework

FIG. 3 illustrates an example machine-learning framework 300 that can be used with examples herein. For example, the implantable stimulator 100, the recipient computing device 160, the server computing device 170, the clinician computing device 180, or another device can store and operate the machine-learning framework 300.

The machine-learning framework 300 is software and associated data that implements machine-learning capabilities. In the illustrated example, the machine-learning framework 300 includes two primary components: a machine-learning model 310 and a machine-learning interface 320. One or more aspects of the machine-learning framework 300 can be implemented with machine-learning toolkits or libraries, such as: TENSORFLOW by GOOGLE INC. of Mountain View, California; OPENAI GYM by OPENAI of San Francisco, California; or MICROSOFT AZURE MACHINE LEARNING by MICROSOFT CORP. of Redmond, Washington The machine-learning model 310 is a structured representation of the learning, such as how learning is achieved and what has been learned. For example, where the machine-learning model 310 includes a neural network, the machine-learning model 310 can define the representation of the neural network (e.g., the nodes of the neural network, the connections between the nodes, the associated weighs, and other data), such as via one or more matrices or other data structures. In another example (e.g., where the machine-learning model 310 includes a decision tree) the machine-learning model 310 can define the decision tree (e.g., the nodes of the decision tree and the connections therebetween). The machine-learning model 310 can include multiple different types of machine-learning techniques. For example, the machine-learning model 310 can define multiple different neural networks, decision trees, and other machine-learning techniques and their connections therebetween. For instance, output of a first neural network can flow to the input of a second neural network with the output therefrom flowing into a decision tree to produce a final output.

The machine-learning interface 320 defines a software interface used in conjunction with the machine-learning model 310. For example, the machine-learning interface 320 can define functions, processes, and interfaces for providing input to, receiving output from, training, and maintaining the machine-learning model 310.

In some examples, the machine-learning interface 320 requires the input data to be preprocessed. In other examples, the machine-learning interface 320 can be configured to perform the preprocessing. The preprocessing can include, for example, placing the input data into a particular format for use by the machine-learning model 310. For instance the machine-learning model 310 can be configured to process input data in a vector format and the data provided for processing can be converted into such a format via the preprocessing. In an example, the interface provides functions that convert the provided data into a useful format and then provide the converted data as input into the machine-learning model 310.

The machine-learning interface 320 can define a training procedure 330 for preparing the machine-learning model 310 for use. The machine-learning framework 300 can be trained or otherwise configured to receive data as input and provide an output based thereon. For example, the machine-learning model 310 can be trained to receive the stimulation data 222 as input and provide, as output, an indication of whether the stimulation data 222 is indicative of the presence of neotissue, such as by providing neotissue formation characteristics 232. In another example, the machine-learning model 310 can be trained to receive the neotissue formation characteristics 232 as input and provide, as output, one or more treatment actions 242 to be performed. The training procedure 330 can begin with operation 332.

Operation 332 includes obtaining training data. The training data is typically a set of human- or machine-curated data having known training input and desired training output usable to train the machine-learning model 310. In examples herein, the training data can include curated stimulation data 222 from many different individuals or artificially-created stimulation data 222 and actual or expected output (e.g., neotissue formation characteristics 232) of the machine-learning model 310 for that data. For example, stimulation data 222 can be obtained from individuals known or suspected to have neotissue formation. The neotissue formation can be confirmed using, for example, medical imaging techniques. In another example, stimulation data 222 can be generated from benchtop or computer simulations of an implantable stimulator 100 being affected by neotissue formation. Following operation 332, the flow can move to operation 334.

Operation 334 includes processing the training data. Processing the training data includes providing the training data as input into the machine-learning model 310. In examples, the training data can be provided as input into the machine-learning model 310 using an associated machine-learning interface 320. Then the machine-learning model 310 processes the input training data to produce an output.

Following operation 334, the flow can move to operation 336. Operation 336 includes obtaining the output from the machine-learning model 310. This can include receiving output from a function that uses the machine-learning model 310 to process input data. Following operation 336, the flow can move to operation 338.

Operation 338 includes calculating a loss value. A loss function can be used to calculate the loss value, such as based on a comparison between the actual output of the machine-learning model 310 and the expected output (e.g., the training output that corresponds to the training input provided). Any of a variety of loss functions can be selected and used, such as mean square error or hinge loss. Attributes of the machine-learning model 310 (e.g., weights of connections in the machine-learning model) can be modified based on the loss value, thereby training the model.

If the loss value is not sufficiently small (e.g., does not satisfy a threshold), then the flow can return to operation 332 to further train the machine-learning model 310. This training process continues for an amount of training data until the loss value is sufficiently small. If the loss value is sufficiently small (e.g., less than or equal to a predetermined threshold), the flow can move to operation 340.

Operation 340 includes completing the training. In some examples, completing the training includes providing the machine-learning framework 300 for use in production. For example, the machine learning framework 300 with the trained machine-learning model 310 can be stored on the implantable stimulator 100, the recipient computing device 160, the server computing device 170, the clinician computing device 180, or at another location for use. In some examples, prior to providing the machine-learning framework 300 for use, the trained machine-learning model 310 is validated using validation input-output data (e.g., data having desired outputs corresponding to particular inputs that are different from the training data), and after successful validation, the machine-learning framework 300 is provided for use.

The above techniques describe a machine-learning approach. Other artificial intelligence techniques can be used in conjunction with technologies herein. For instance, human-generated or curated artificial intelligence frameworks can be constructed that are configured to receive stimulation data 222 or other input and provide, as output, an indication of whether neotissue exists or particular treatment actions that should be taken. Such artificial intelligence techniques can include, for example, decision trees, thresholding, heuristics, scoring, other techniques, or combinations thereof.

Example Computing System

Figure 4:
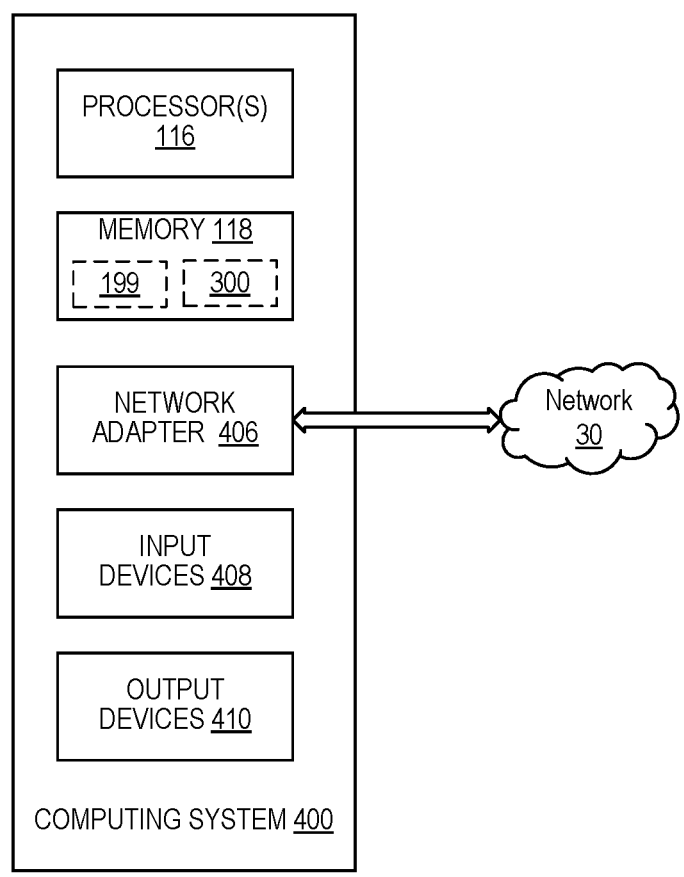
FIG. 4 illustrates an example of a suitable computing system with which one or more of the disclosed examples can be implemented

FIG. 4 illustrates an example of a suitable computing system 400 with which one or more of the disclosed examples can be implemented. Computing systems, environments, or configurations that can be suitable for use with examples described herein include, but are not limited to, personal computers, server computers, hand-held devices, laptop devices, multiprocessor systems, microprocessor-based systems, programmable consumer electronics (e.g., smart phones), network PCs, minicomputers, mainframe computers, tablets, distributed computing environments that include any of the above systems or devices, and the like. The computing system 400 can be a single virtual or physical device operating in a networked environment over communication links to one or more remote devices. In examples, the recipient computing device 160, the clinician computing device 180, and the server computing device 170 includes one or more components or variations of components of the computing system 400. Further, in some examples, the implantable stimulator 100 includes one or more components of the computing system 400.

In its most basic configuration, computing system 400 includes one or more processors 116 and memory 118.

As described above, the one or more processors 116 can include one or more hardware or software processors (e.g., Central Processing Units) that can obtain and execute instructions. The one or more processors 116 can communicate with and control the performance of other components of the computing system 400.

As described above, the memory 118 can be one or more software- or hardware-based computer-readable storage media operable to store information accessible by the one or more processors 116. As implemented in the computing system 400, the memory 118 can be configured to store, among other things, instructions executable by the one or more processors 116 to implement applications or cause performance of operations described herein, as well as other data. The memory 118 can be volatile memory (e.g., RAM), non-volatile memory (e.g., ROM), or combinations thereof. The memory 118 can include transitory memory or non-transitory memory. The memory 118 can also include one or more removable or non-removable storage devices. In examples, the memory 118 can include RAM, ROM, EEPROM, flash memory, optical disc storage, magnetic storage, solid state storage, or any other memory media usable to store information for later access. In examples, the memory 118 encompasses a modulated data signal (e.g., a signal that has one or more of its characteristics set or changed in such a manner as to encode information in the signal), such as a carrier wave or other transport mechanism and includes any information delivery media. By way of example, and not limitation, the memory 118 can include wired media such as a wired network or direct-wired connection, and wireless media such as acoustic, RF, infrared and other wireless media or combinations thereof.

In the illustrated example, the computing system 400 further includes a network adapter 406, one or more input devices 408, and one or more output devices 410. The computing system 400 can include other components, such as a system bus, component interfaces, a graphics system, a power source (e.g., a battery), among other components.

The network adapter 406 is a component of the computing system 400 that provides network access. Network access can include access to the network 30. The network adapter 406 can provide wired or wireless network access and can support one or more of a variety of communication technologies and protocols, such as ETHERNET, cellular, BLUETOOTH, near-field communication, and RF (Radiofrequency), among others. The network adapter 406 can include one or more antennas and associated components configured for wireless communication according to one or more wireless communication technologies and protocols.

The one or more input devices 408 are devices over which the computing system 400 receives input from a user. The one or more input devices 408 can include physically-actuatable user-interface elements (e.g., buttons, switches, or dials), touch screens, keyboards, mice, pens, and voice input devices, among others input devices.

The one or more output devices 410 are devices by which the computing system 400 is able to provide output to a user. The output devices 410 can include, displays, speakers, and printers, among other output devices.

Example Devices

As previously described, the technology disclosed herein can be applied in any of a variety of circumstances and with a variety of different devices. Example devices that can benefit from technology disclosed herein are described in more detail in FIGS. 5 and 6, below. For example, the implantable stimulator 100 can be part of an auditory prosthesis, such as a cochlear implant as described in FIG. 5. As another example, implantable stimulator 100 can be a retinal prosthesis, such as is described in FIG. 6. The technology can be applied to other medical devices, such as neurostimulators, cardiac pacemakers, cardiac defibrillators, sleep apnea management stimulators, seizure therapy stimulators, tinnitus management stimulators, and vestibular stimulation devices, as well as other medical devices that deliver stimulation to tissue. These different medical devices can be implemented as implantable stimulators and can benefit from use with the systems and processes described above.

Example Sensory Prostheses—Cochlear Implant System

Figure 5:
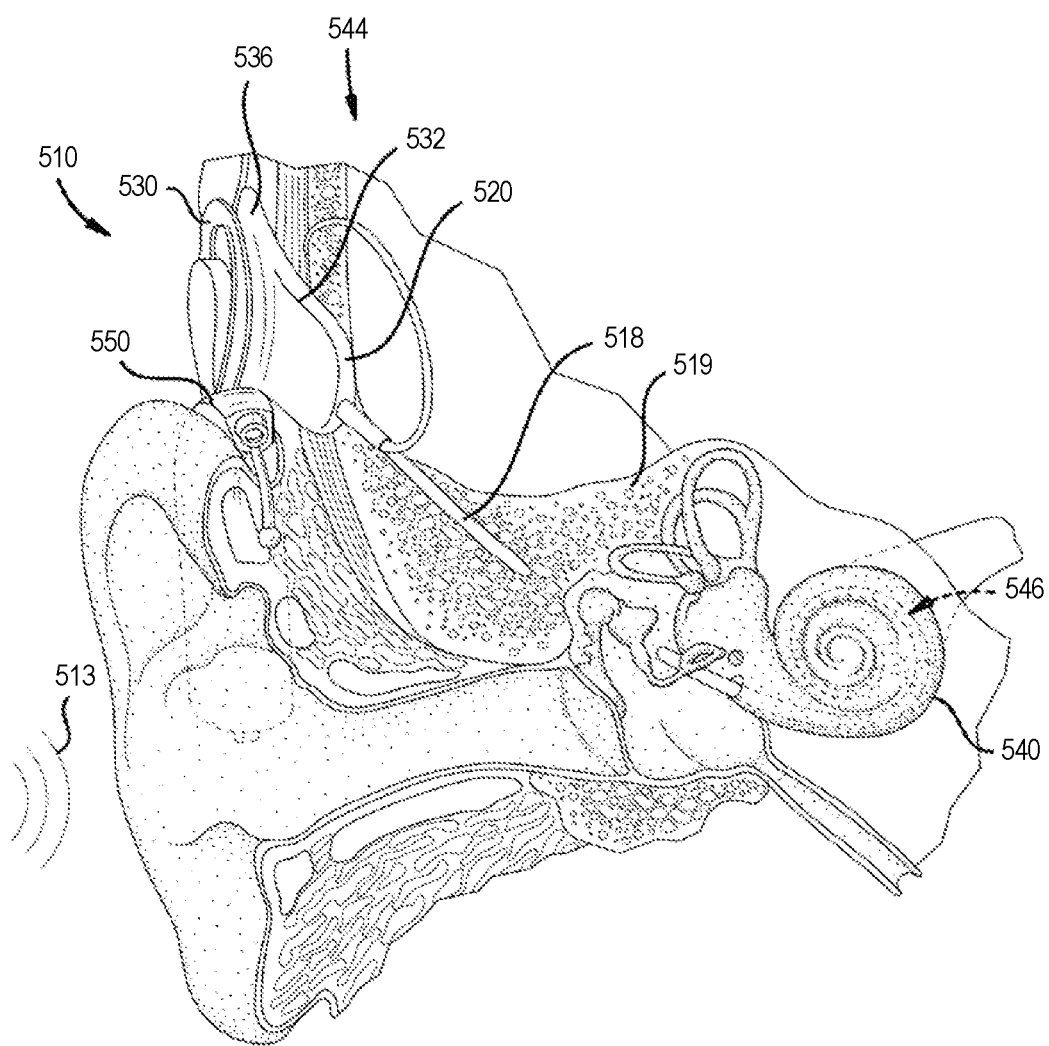
FIG. 5 illustrates an example cochlear implant system that can benefit from use of the technologies disclosed herein.

FIG. 5 illustrates an example cochlear implant system 510 that can benefit from use of the technologies disclosed herein. The cochlear implant system 510 includes an implantable component 544 typically having an internal receiver/transceiver 532, a stimulator unit 520, and an elongate lead 518. The internal receiver/transceiver 532 permits the cochlear implant system 510 to receive signals from and/or transmit signals to an external device 550. The external device 550 can be a button sound processor worn on the head that includes a receiver/transceiver coil 530 and sound processing components. Alternatively, the external device 550 can be just a transmitter/transceiver coil in communication with a behind-the-ear device that includes the sound processing components and microphone.

The implantable component 544 includes an internal coil 536, and preferably, a magnet (not shown) fixed relative to the internal coil 536. The magnet can be embedded in a pliable silicone or other biocompatible encapsulant, along with the internal coil 536. Signals sent generally correspond to external sound 513. The internal receiver/transceiver 532 and the stimulator unit 520 are hermetically sealed within a biocompatible housing, sometimes collectively referred to as a stimulator/receiver unit. Included magnets (not shown) can facilitate the operational alignment of an external coil 530 and the internal coil 536, enabling the internal coil 536 to receive power and stimulation data from the external coil 530. The external coil 530 is contained within an external portion. The elongate lead 518 has a proximal end connected to the stimulator unit 520, and a distal end 546 implanted in a cochlea 540 of the recipient. The elongate lead 518 extends from stimulator unit 520 to the cochlea 540 through a mastoid bone 519 of the recipient. The elongate lead 518 is used to provide electrical stimulation to the cochlea 540 based on the stimulation data. The stimulation data can be created based on the external sound 513 using the sound processing components.

In certain examples, the external coil 530 transmits electrical signals (e.g., power and stimulation data) to the internal coil 536 via a radio frequency (RF) link. The internal coil 536 is typically a wire antenna coil having multiple turns of electrically insulated single-strand or multi-strand platinum or gold wire. The electrical insulation of the internal coil 536 can be provided by a flexible silicone molding. Various types of energy transfer, such as infrared (IR), electromagnetic, capacitive and inductive transfer, can be used to transfer the power and/or data from external device to cochlear implant. While the above description has described internal and external coils being formed from insulated wire, in many cases, the internal and/or external coils can be implemented via electrically conductive traces.

Example Medical Device—Retinal Prosthesis

Figure 6:
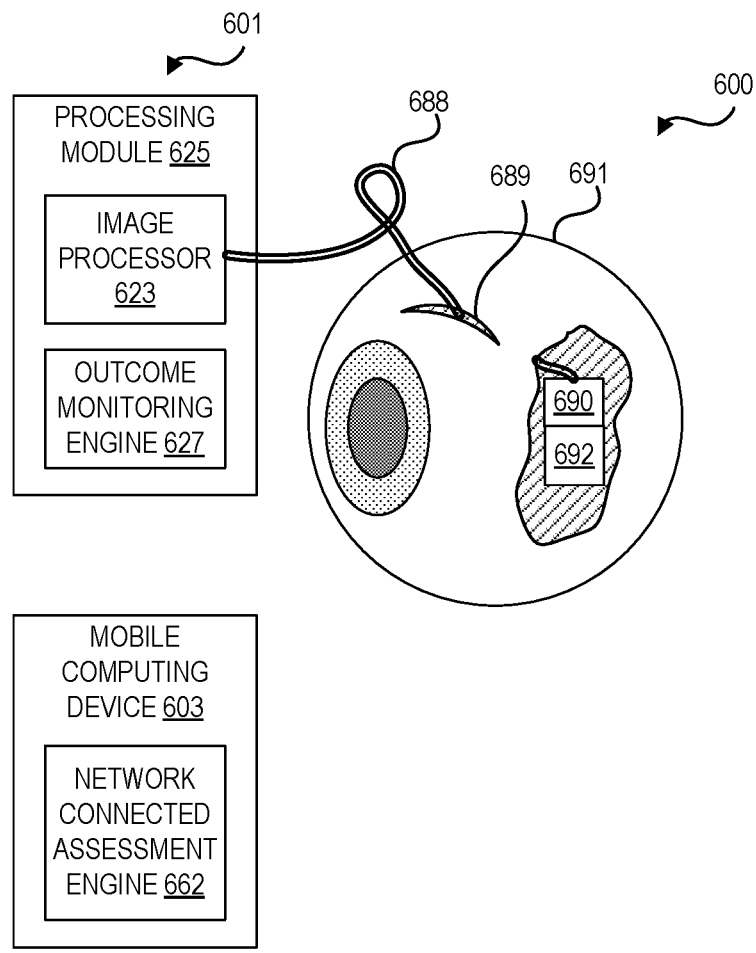
FIG. 6 illustrates a retinal prosthesis system that comprises a retinal prosthesis and a mobile computing device.

FIG. 6 illustrates a retinal prosthesis system 601 that comprises a retinal prosthesis 600 and a mobile computing device 603. The retinal prosthesis 600 comprises a processing module 625 and a retinal prosthesis sensor-stimulator 690 is positioned proximate the retina 691 of a recipient. In an example, sensory inputs (e.g., photons entering the eye) are absorbed by a microelectronic array of the sensor-stimulator 690 that is hybridized to a glass piece 692 including, for example, an embedded array of microwires. The glass can have a curved surface that conforms to the inner radius of the retina. The sensor-stimulator 690 can include a microelectronic imaging device that can be made of thin silicon containing integrated circuitry that convert the incident photons to an electronic charge.

The processing module 625 includes an image processor 623 that is in signal communication with the sensor-stimulator 690 via, for example, a lead 688 which extends through surgical incision 689 formed in the eye wall. In other examples, processing module 625 can be in wireless communication with the sensor-stimulator 690. The image processor 623 processes the input into the sensor-stimulator 690, and provides control signals back to the sensor-stimulator 690 so the device can provide an output to the optic nerve. That said, in an alternate example, the processing is executed by a component proximate to, or integrated with, the sensor-stimulator 690. The electric charge resulting from the conversion of the incident photons is converted to a proportional amount of electronic current which is input to a nearby retinal cell layer. The cells fire and a signal is sent to the optic nerve, thus inducing a sight perception.

The processing module 625 may be implanted in the recipient or may be part of an external device, such as a Behind-The-Ear (BTE) unit, a pair of eyeglasses, etc. The retinal prosthesis 600 can also include an external light/image capture device (e.g., located in/on a BTE device or a pair of glasses, etc.), while, as noted above, in some examples, the sensor-stimulator 690 captures light/images, which sensor-stimulator is implanted in the recipient.

Similar to the above examples, the retinal prosthesis system 601 may be used in spatial regions that have at least one controllable network connected device associated therewith (e.g., located therein). As such, the processing module 625 includes a performance monitoring engine 627 that is configured to obtain data relating to a "sensory outcome" or "sensory performance" of the recipient of the retinal prosthesis 600 in the spatial region. As used herein, a "sensory outcome" or "sensory performance" of the recipient of a sensory prosthesis, such as retinal prosthesis 600, is an estimate or measure of how effectively stimulation signals delivered to the recipient represent sensor input captured from the ambient environment.

Data representing the performance of the retinal prosthesis 600 in the spatial region is provided to the mobile computing device 603 and analyzed by a network connected device assessment engine 662 in view of the operational capabilities of the at least one controllable network connected device associated with the spatial region. For example, the network connected device assessment engine 662 may determine one or more effects of the controllable network connected device on the sensory outcome of the recipient within the spatial region. The network connected device assessment engine 662 is configured to determine one or more operational changes to the at least one controllable network connected device that are estimated to improve the sensory outcome of the recipient within the spatial region and, accordingly, initiate the one or more operational changes to the at least one controllable network connected device.

As should be appreciated, while particular uses of the technology have been illustrated and discussed above, the disclosed technology can be used with a variety of devices in accordance with many examples of the technology. The above discussion is not meant to suggest that the disclosed technology is only suitable for implementation within systems akin to that illustrated in the figures. For examples, while certain technologies described herein were primarily described in the context of auditory prostheses (e.g., cochlear implants), technologies disclosed herein are applicable to medical devices generally (e.g., medical devices providing pain management functionality or therapeutic electrical stimulation, such as deep brain stimulation). In general, additional configurations can be used to practice the processes and systems herein and/or some aspects described can be excluded without departing from the processes and systems disclosed herein. Further, the techniques described herein can be applicable to determining a recipient's response to other stimuli, such as visual stimuli, tactile stimuli, olfactory stimuli, taste stimuli, or another stimuli. Likewise, the devices used herein need not be limited to auditory prostheses and can be other medical devices configured to support a human sense, such as bionic eyes.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and processes to the particular aspects described. Accordingly, additional configurations can be used to practice the methods and systems herein and/or some aspects described can be excluded without departing from the methods and systems disclosed herein.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure. Further, the disclosed processes can be repeated.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

What is claimed is:

1. A system, comprising:
   a stimulator assembly having one or more electrodes;
   a biocompatible housing connected to the stimulator assembly;
   a stimulation source disposed in the biocompatible housing and configured to deliver electrical stimulation to target tissue of a recipient via the one or more electrodes; and
   one or more processors configured to:
      generate a current flow path using the one or more electrodes for stimulating tissue;
      measure one or more transimpedance matrices for the one or more electrodes based on the current flow path;
      determine neotissue formation characteristics relating to tissue growth proximate the one or more electrodes based on the one or more transimpedance matrices;
      determine a treatment modification instruction to modify stimulation parameters to account for the tissue growth; and
      apply the treatment modification instruction to modify ongoing stimulation provided by the apparatus.

2. The system of claim 1, wherein to apply the treatment modification instruction to modify ongoing treatment provided by the apparatus includes to:
   modify a threshold stimulation level provided by the stimulation source; and
   modify a maximum stimulation level provided by the stimulation source.

3. The system of claim 1, wherein to apply the treatment modification instruction to modify ongoing treatment provided by the apparatus includes to:
   disable at least one of the one or more electrodes.

4. The system of claim 1, wherein the one or more transimpedance matrices are based on a polarity of current flow, a phase width timing, or a stimulus intensity.

5. The system of claim 1, wherein to measure the one or more transimpedance matrices includes to:
   measure a transimpedance matrix at multiple times during a stimulation pulse or to measure a transimpedance matrix longitudinally.

6. The system of claim 1, wherein to measure one or more characteristics relating to the current flow path to generate stimulation data includes measuring at least one of voltage profile data, evoked compound action potential data, electrical field imaging data, or electrical sounding data.

7. A method comprising:
   determining a transimpedance matrix for a plurality of electrodes of an implanted stimulator;
   detecting neotissue formation characteristics proximate at least one of the plurality of electrodes based on the transimpedance matrix; and
   performing a treatment action based on the neotissue formation characteristics.

8. The method of claim 7, wherein determining the transimpedance matrix includes:
   causing a current flow path to be generated from an active electrode of the plurality of electrodes of the implanted stimulator through tissue of a recipient of the implanted stimulator, wherein the tissue includes neotissue growth proximate the active electrode that occurred since implantation of the implanted stimulator.

9. The method of claim 8, wherein causing the current flow path to be generated includes:
   forming the current flow path from the active electrode to a return electrode of the implanted stimulator.

10. The method of claim 7, wherein performing the treatment action includes:
    administering a therapeutically-effective amount of an anti-inflammatory drug to a recipient of the implanted stimulator to reduce neotissue growth or resist formation of unwanted tissue growth proximate the plurality of electrodes.

11. The method of claim 7, wherein detecting neotissue formation characteristics includes:
    determining a metric estimating an extent of tissue growth proximate one or more electrodes of the implanted stimulator.

12. The method of claim 7, wherein performing the treatment action includes:
    modifying maximum or minimum stimulation thresholds for one or more electrodes of the implanted stimulator.

13. The method of claim 7, wherein the detecting neotissue formation characteristics is further based on at least one of measured electrically-evoked compound action potential data, measured voltage profile data, measured evoked compound action potential data, measured electrical field imaging data, or measured electrical sounding data.

14. A system comprising: one or more processors; and a non-transitory computer-readable memory comprising instructions that, when executed, cause the one or more processors to: obtain a transimpedance matrix for a plurality of electrodes of an implanted stimulator; determine neotissue formation characteristics relating to tissue growth proximate one or more electrodes of the implanted stimulator based on the transimpedance matrix, determine a treatment modification to modify stimulation parameters of the implanted stimulator to account for the tissue growth, and apply the treatment modification to the implanted stimulator to modify ongoing stimulation provided by the implanted stimulator.

15. The system of claim 14, wherein to determine the neotissue formation characteristics includes to: extract, from stimulation data of the implanted stimulator, indications of a local voltage field around an electrode associated with a current flow path, wherein determining the neotissue formation characteristics includes processing the indications.

16. The system of claim 14, wherein to determine the neotissue formation characteristics includes to: determine whether stimulation data regarding the implanted stimulator satisfies one or more thresholds.

17. The system of claim 14, wherein to determine the neotissue formation characteristics includes to: provide stimulation data regarding the implanted stimulator as input parameters into a decision tree procedure or a trained machine learning procedure.

18. The system of claim 14, wherein the instructions further cause the one or more processors to: obtain medical imaging data associated with the implanted stimulator, wherein the neotissue formation characteristics are further generated based on the medical imaging data.

19. The system of claim 14, wherein determining neotissue formation characteristics includes providing stimulation data as input to a machine-learning framework and obtaining output from the machine-learning framework.

* * * * *